(12) United States Patent
Fujikawa et al.

(10) Patent No.: US 6,187,049 B1
(45) Date of Patent: Feb. 13, 2001

(54) CERAMIC FEMUR HEAD FOR ARTIFICIAL JOINT

(75) Inventors: Kentaro Fujikawa; Eiji Miyata, both of Aichi (JP)

(73) Assignee: NGK Spark Plug Co., Ltd., Nagoya (JP)

( * ) Notice: Under 35 U.S.C. 154(b), the term of this patent shall be extended for 0 days.

(21) Appl. No.: 09/116,942

(22) Filed: Jul. 17, 1998

(30) Foreign Application Priority Data

Jul. 17, 1997 (JP) ........................................ 9-192811

(51) Int. Cl.⁷ ........................................ A61F 2/36
(52) U.S. Cl. ........................................ 623/22; 623/23
(58) Field of Search ........................................ 673/16, 18, 19, 673/20, 22, 23

(56) References Cited

U.S. PATENT DOCUMENTS 5,181,929 * 1/1993 Prats et al. ........................ 623/23
5,871,547 * 2/1999 Abouaf et al. ..................... 623/22

FOREIGN PATENT DOCUMENTS 2-280746 * 11/1990 (JP) .

* cited by examiner

*Primary Examiner*—David J. Isabella
(74) *Attorney, Agent, or Firm*—Foley & Lardner

(57) ABSTRACT

A ceramic femur head is nearly spherical and has a planar end surface. The femur head has a diametric, tapered hole which extends from the planar surface in a way as to taper toward an inner end thereof and in which a correspondingly tapered stem portion of a metallic stem is fitted. The inner peripheral surface of the tapered hole of the ceramic femur head is ground so as to have the same degree of surface finish as that of an outer peripheral surface of the tapered stem portion. For example, in case the outer peripheral surface of the tapered stem portion of the metallic stem is finished to have a surface roughness in the range from 0.1 to 0.6 μm Ra, the surface roughness of the inner peripheral surface of the tapered hole of the ceramic femur head is set to be in the range from 0.1 to 0.6 μm Ra.

5 Claims, 4 Drawing Sheets

CERAMIC FEMUR HEAD FOR ARTIFICIAL JOINT

BACKGROUND OF THE INVENTION

1. Field of the Invention

The present invention relates to a ceramic femur head for use in an artificial joint such as an artificial hip joint (coxa), artificial shoulder joint or the like for human being. The present invention further relates a femur system using such a ceramic femur head.

2. Description of the Related Art

An example of a prior art artificial hip joint is shown in FIG. 5. In FIG. 5, an artificial hip joint is generally designated by 100 and shown as including a femur head 101 constituting part of a sliding joint, a metallic stem 102 embedded in a femur or thighbone to attach the femur head 101 to a hipbone side end F of the thighbone and a socket 103 made of a high density polyethylene (hereinafter referred to as PE) and fixed to a highbone M side. The femur head 101 is slidably received in the socket 103.

The femur head 101 has a sufficient strength for practical use and thus has been used to effect a good result but has a problem of being relatively smaller in strength as compared with a metallic femur head.

As a countermeasure for solving this problem, a study has been made for applying a method of increasing the retaining or holding strength in a tapered fit system (i.e., a kind of press fitting in which joining surfaces are tapered correspondingly) which is frequently seen in machine tools, to an artificial joint. That is, in machine tools, it is known that the holding or retaining strength become larger as the finish of the fitting or joining surface becomes higher, so it is considered desirable in the artificial joint to make the degree of finish as high as possible i.e., make the surface roughness as small as possible (so long as the cost permits).

For this reason, the tapered portion 102a of the metallic stem 102 and the tapered hole 101a of the ceramic femur head 101 are subjected to surface grinding or the like so as to have a higher degree of surface finish, i.e., a smaller surface roughness. In this instance, due to the complicated shape, the tapered portion 102a of the metallic stem 102 is generally lower in the degree of surface finish than the tapered hole 101a of the ceramic femur head 101.

However, the femur head 101 having fitted therein the metallic stem 102 reduces markedly in the fracture strength as it reduces in size, i.e., in diameter, notwithstanding the above described countermeasure, so it has been difficult to make such a ceramic femur head 101 that has a sufficiently large strength for its size.

SUMMARY OF THE INVENTION

According to a first aspect of the present invention, there is provided a novel and improved femur system which comprises a ceramic femur head having a taper hole, and a stem having a tapered stem portion fitted in said tapered hole of said ceramic femur head. An inner peripheral surface of the tapered hole of the ceramic femur head has substantially the same surface roughness as an outer peripheral surface of the tapered stem portion of the stem.

The above described stem is a stem-like member which is attached to a thighbone and to which is fitted the femur head.

As the material of the stem, a metal which is softer than the ceramic femur head is desirable since a stem made of such a metal exhibits a good conformability when fitted in the femur head. For example, Ti, Ti alloy, stainless steel, Co—Cr alloy and the like are particularly desirable since they have a good biological affinity and durability and furthermore can reduce the cost.

As the material of the above described ceramic femur head, a ceramic containing, for example, $Al_2O_3$, $ZrO_2$, $Si_3N_4$ SiC or the like can be used.

By the first aspect of the invention, the ceramic femur head and the stem can be fitted at their tapered portions smoothly and furthermore can be joined in a way as to increase their contact area since the inner peripheral surface of the tapered hole of the ceramic femur head and the outer peripheral surface of the tapered portion of the stem are finished so as to have substantially the same surface roughness. By this, the femur head and the stem are connected or united together firmly, thus resultantly enabling the femur head to have a sufficient strength even in case it is reduced in size.

Heretofore, it has been practiced to finish the stem and the femur head in such a manner that the femur head has a smaller surface roughness than the stem. By the experiments conducted by the applicants, it was revealed and discovered that a higher compression rupture strength can be attained when the stem and the femur head are finished so as to have the same surface roughness, and based on this discovery the present invention was made.

As the reason why such a result was attained, it is considered that a higher degree of surface finish (i.e., a smaller surface roughness) of the tapered hole of the ceramic femur head rather results in an actually reduced contact area with the stem and reversely a lower degree of surface finish (i.e., a larger surface roughness) on the femur head side than the conventional can increase the contact area. For example, as shown in FIG. 1A, in case the surface roughness on the femur head side is smaller than that on the stem side, the surface irregularities of the stem are conformed to the surface of the femur head which has a larger hardness, resulting in a small contact leading to an increased stress per unit area and therefore a lowered strength. In contrast to this, in case the surface roughness of the femur head is not so small and nearly equal to that on the stem side, the surface irregularities of the stem are fitted or engaged in those of the femur head as shown in FIG. 1b when the stem is pressed into the femur head, resulting in a large contact area leading to a reduced stress per unit area and therefore a higher strength.

On the other hand, in case the surface roughness on the stem side is too large as compared with that on the femur head side, i.e., the surface of the stem is too rough, smooth fitting of the stem and the femur head at their tapered portions cannot be attained but the stress resulting at the time of their press fitting may be concentrated at a unexpected place to possibly cause breakage of the femur head, so such a stem is not desirable.

In the meantime, in case the degree of surface finish on the stem side is considerably high as compared with that on the femur head side, it is considered that fitting of the stem and femur head at their tapered portions is so smooth as to reversely reduce the contact area, so such a stem is not desirable.

Further, the present invention does not require excessive surface grinding of the tapered hole of the ceramic femur head as the conventional but makes it possible to rather lower its degree of surface finish than the conventional. Thus, the present invention has an advantage of contributing to reduction of the cost.

According to a second aspect of the present invention, the difference in the surface roughness between the outer peripheral surface of the tapered stem portion of the stem and the inner peripheral portion of the tapered hole of the ceramic femur head is equal to or larger than 1 μm Ra.

Ra which represents a degree of surface finish is a center line average roughness Ra which is defined according to JIS 0601.

By the second aspect, the difference in the degree of surface finish between the tapered stem portion of the stem and the tapered hole of the femur head is small, i.e., 1 μm Ra or less. When the difference is in such a range, a sufficiently large contact area between the femur head and the stem can be attained at the time of fitting at their tapered portions, thus making it possible to attain a large compression rupture strength and smooth fitting of the tapered portions.

According to a third aspect of the present invention, the difference in the surface roughness between the outer peripheral surface of the tapered stem portion of the stem and the inner peripheral portion of the tapered hole of the ceramic femur head is equal to or larger than 10 μm Rmax.

Rmax which represents the degree of surface finish is maxim height Rmax which is defined according to JIS 06101.

By the third aspect, the difference in the degree of surface finish between the tapered stem portion of the stem and the tapered hole of the femur head is small, i.e., 10 μm Rmax or less. When the difference is in such a range, a sufficiently large contact area between the femur head and the stem can be attained at the time of fitting at their tapered portions, thus making it possible to attain a large compression rupture strength and smooth fitting of the tapered portions.

According to a fourth aspect of the present invention, the inner peripheral surface of the tapered hole of the ceramic femur head has a surface roughness in the range from 0.05 to 1.0 μm Ra.

By the fourth aspect, the tapered hole of the femur head is finished so as to have the surface roughness in the range from 0.05 to 1.0 μm Ra, so a large compression rupture strength can be attained and furthermore their fitting at their tapered portions can be smooth.

In this connection, in case the surface roughness is smaller than 0.5 m Ra, the surface on the femur head side becomes excessively smooth and its surface irregularities become too small, thus causing the contact area at the time of their fitting at their tapered portions to become small as described above. Thus, such a small surface roughness is not desirable. On the other hand, in case the surface roughness is larger than 1.0 μm Ra, the surface on the femur head side becomes so rough that it is difficult to attain smooth fitting and breakage of the femur head may occur in some case. Thus, such a large surface roughness is not desirable.

That is, in case the surface roughness is in the range according to the fourth aspect, smooth fitting at their tapered portions can be attained while at the same time a large contact area can be obtained, whereby it becomes possible to realize a high compression rupture strength. Thus, such a surface roughness range is desirable.

According to a fifth aspect of the present invention, the inner peripheral surface of the tapered hole of the ceramic femur head has a surface roughness in the range from 0.5 to 10 μm Rmax.

In case the surface roughness is smaller than 0.5 μm Rmax, the surface on the femur head side becomes too smooth and its surface irregularities become too small, similarly to the case of the fourth aspect, thus causing the contact area at the time of their fitting at their tapered portions to become small as described above. Thus, such a small surface roughness is not desirable. On the other hand, in case the surface roughness is larger than 10 μm Ra, the surface on the femur head side becomes so rough that it is difficult to attain smooth fitting and breakage of the femur head may occur in some case. Thus, such a large surface roughness is not desirable.

That is, in case the surface roughness is in the range according to the fifth aspect, smooth fitting at their tapered portions can be attained while at the same time a large contact area can be obtained, whereby it becomes possible to realize a high compression rupture strength. Thus, such a surface roughness range is desirable.

According to the sixth to tenth aspects, there is provided an artificial joint including a femur head system of the character as described with respect to the first to fifth aspects. By this aspects, the artificial joint can attain a sufficiently large compression rupture strength for its size and it becomes possible to realize a high reliable artificial joint.

The above structure is effective for solving the above noted problems inherent in the prior art device.

It is accordingly an object of the present invention to provide a ceramic femur head for an artificial joint which can be produced at a low cost and has a high strength even if it is small in diameter, i.e., small-sized.

It is another object of the present invention to provide a novel and improved femur system having a ceramic femur head of the foregoing character.

It is a further object of the present invention to provide a novel and improved artificial joint including a femur system of the foregoing character.

DETAILED DESCRIPTION OF THE DRAWINGS

Figure 1A:
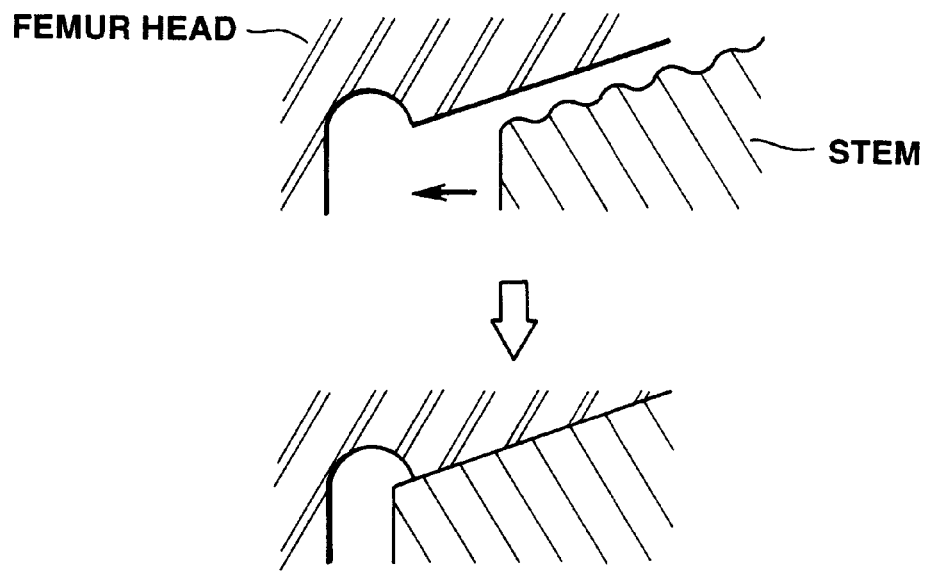
FIGS. 1A and 1B are illustrations of a principle of a ceramic femur head of the present invention.
Figure 1B:
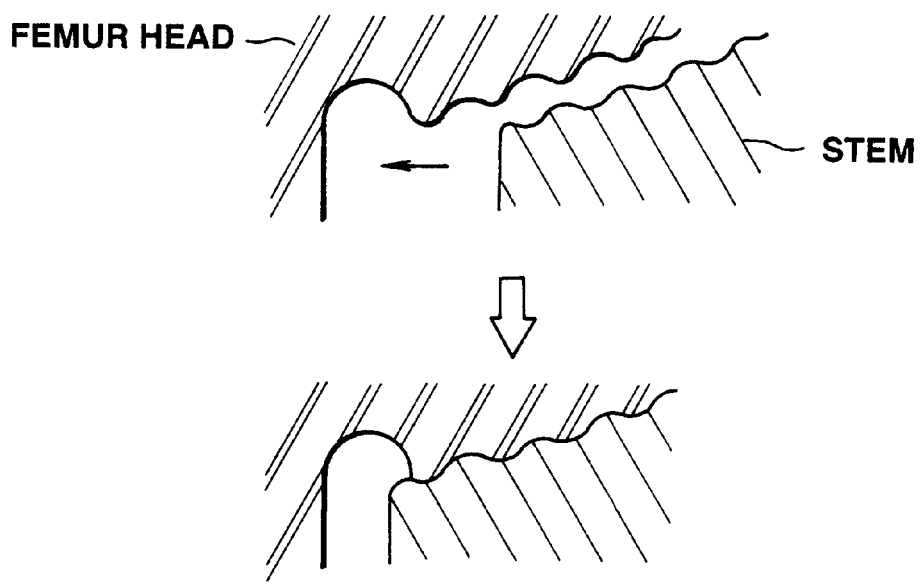
Figure 2:
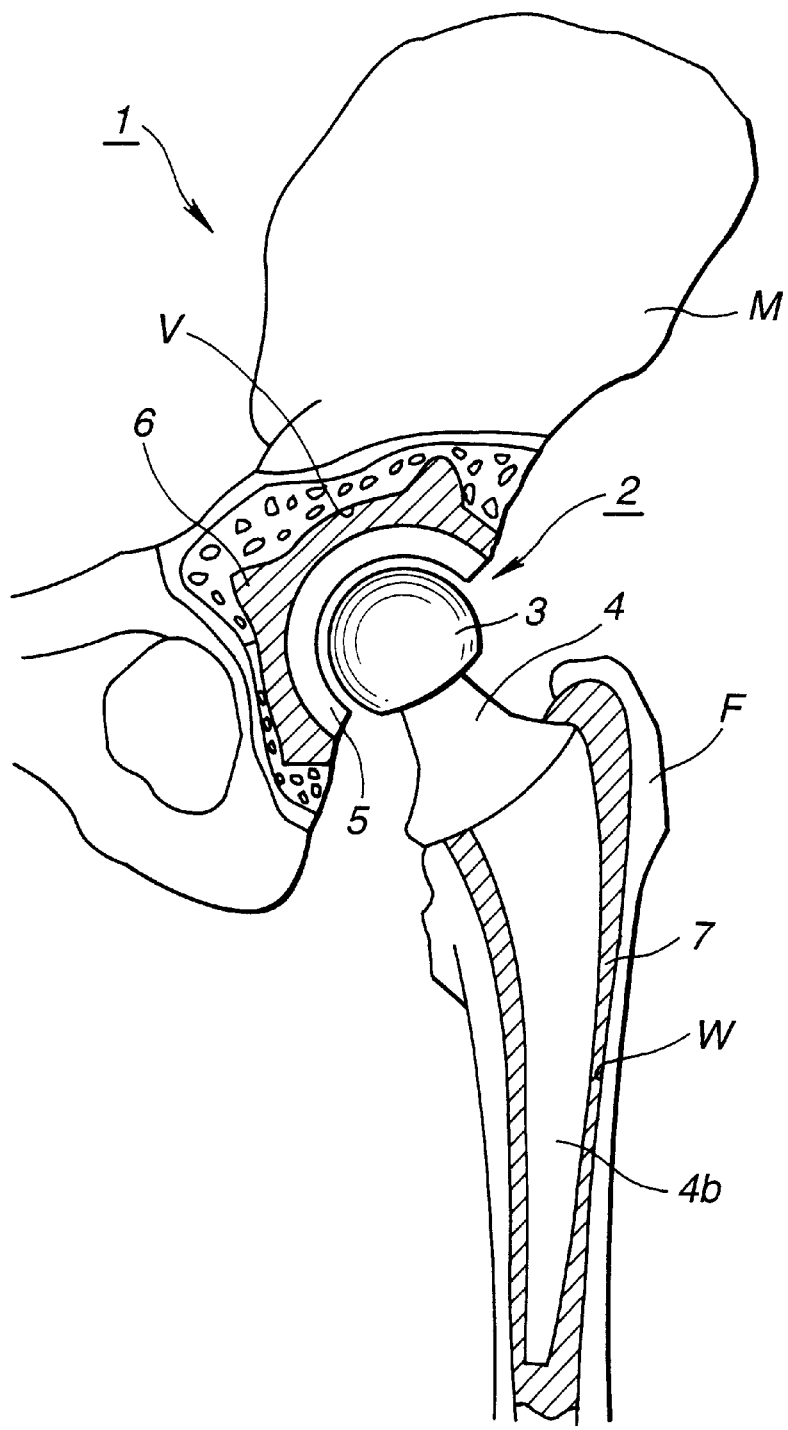
FIG. 2 is a sectional view of an artificial joint incorporating a ceramic femur head according to an embodiment of the present invention.
Figure 3:
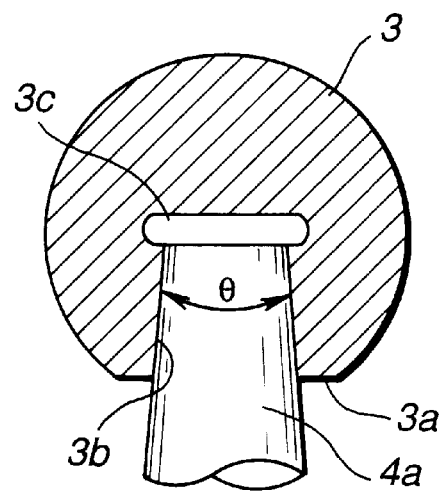
FIG. 3 is an enlarged sectional view of the ceramic femur head of FIG. 2, together with the stem.

Referring to FIGS. 1 to 3 inclusive, an artificial joint incorporating a ceramic femur head system according to an embodiment of the present invention will be described.

In FIG. 2, an artificial joint is generally indicated by 1 and shown as including a femur head system constructed of a ceramic femur head 3 and a metallic stem 4 fitted at an end to the ceramic femur head 3, and a socket 5 made of polyethylene (PE), fixedly attached to the hipbone M side and receiving the ceramic femur head.

The above described metallic stem 4 is made of a metal selected from the group consisting of Ti, Ti alloy, stainless steel and Co—Cr alloy. As shown in FIG. 3, the metallic stem 4 has a tapered end portion 4a which tapers toward a terminal end and is fitted in the ceramic femur head 3 and another end portion 4b which becomes slender gradually toward an end and is fixedly held in a hole W formed by cutting of a bone, by way of a bone cement layer 7. In the meantime, the tapered end portion 4a is 10 mm in diameter at the terminal end thereof and tapers at an angle θ.

On the other hand, the socket 5 has a part-spherical inner surface and is fixedly held in a recess V which is formed by cutting of a bone, by way of a bone cement layer 6.

Further, the ceramic femur head 3 is constituted by a sintered ceramic body containing, for example $Al_2O_3$, $ZrO_2$, $Si_3N_4$, SiC, or the like as a major component.

The ceramic femur head 3 is nearly spherical and has a planar end surface 3a as shown in FIG. 3. The ceramic femur head 3 is formed with a diametric, tapered hole 3b extending from the planar surface 3a in a way as to taper toward an inner end thereof. Further, the taper hole 3b has at the inner end thereof a clearance hole section 3c. In the meantime, the ceramic femur head 3 is 26 mm in diameter, the taper hole 3b is 10 mm in depth, and the taper angle θ of the taper hole 3b is 6°, correspondingly to the tapered portion 4a of the metallic stem 4.

In manufacture of the ceramic femur head 3, $Al_2O_3$ powder is formed into a predetermined shape corresponding to that of the ceramic femur head 3 by pressing and then sintered. In a final step, the sintered femur head 3 is subjected to surface grinding.

Particularly, in this embodiment, the inner peripheral surface of the tapered hole 3b of the ceramic femur head 3 is ground so as have the same degree of surface finish (i.e., the same surface roughness) as that of the outer peripheral surface of the tapered portion 4a of the metallic stem 4. For example, in the case the outer peripheral surface of the tapered portion 4a of the metallic stem 4 is of such a degree of surface finish that causes its surface roughness to be in the range from 0.1 to 0.6 μm Ra, the degree of surface finish of the inner peripheral surface of the ceramic femur head 3 is set so that its surface roughness is in the range from 0.1 to 0.6 μm Ra.

Since in this embodiment the outer peripheral surface of the tapered portion 4a of the metallic stem 4 is nearly the same in the degree of surface finish as the tapered hole 3b of the ceramic femur head 3 in the above described manner, a larger contact area between them and a larger compression strength comes larger of the joint can be attained. Further, the tapered portion 4a of the metallic stem 4 can be fitted in the tapered hole 3b of the ceramic femur head 3 smoothly, so that breakage of the ceramic femur head 3 at the time of its fitting is hard to occur.

(Experiment)

The experiment which was conducted for confirming the effect of the embodiment of the present invention will be described.

As shown in Tables 1 and 2, various examples of femur heads according to this embodiment (example Nos. 1–12) and comparative examples (example Nos. 13–16) were produced. In the meantime, in Tables 1 and 2, the degree of surface finish is the average of measurement values at four places which was determined at random.

By fitting stems of various materials (having such a shape as shown in the above described embodiment) into the tapered holes of the examples of ceramic femur head, inspection was made as to the fitting condition, i.e., whether the fitting was attained smoothly and whether any breakage was caused at the time of fitting. The result was described in Table 3.

Figure 4:
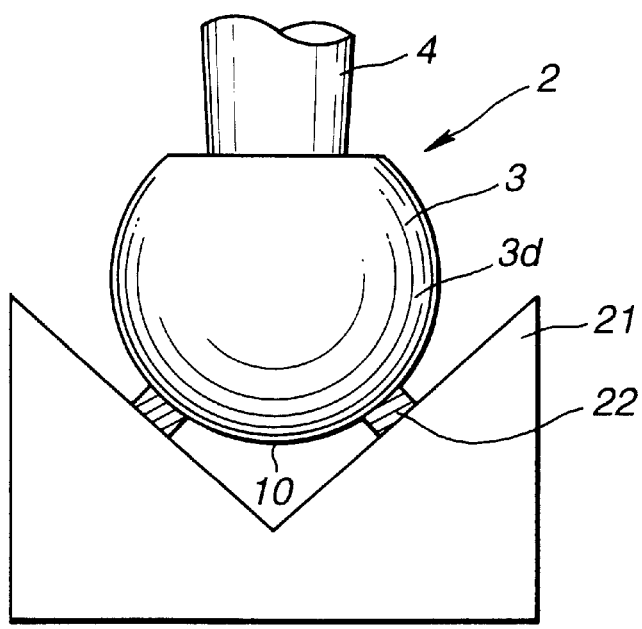
FIG. 4 is an illustration of an experimental method.
Figure 5:
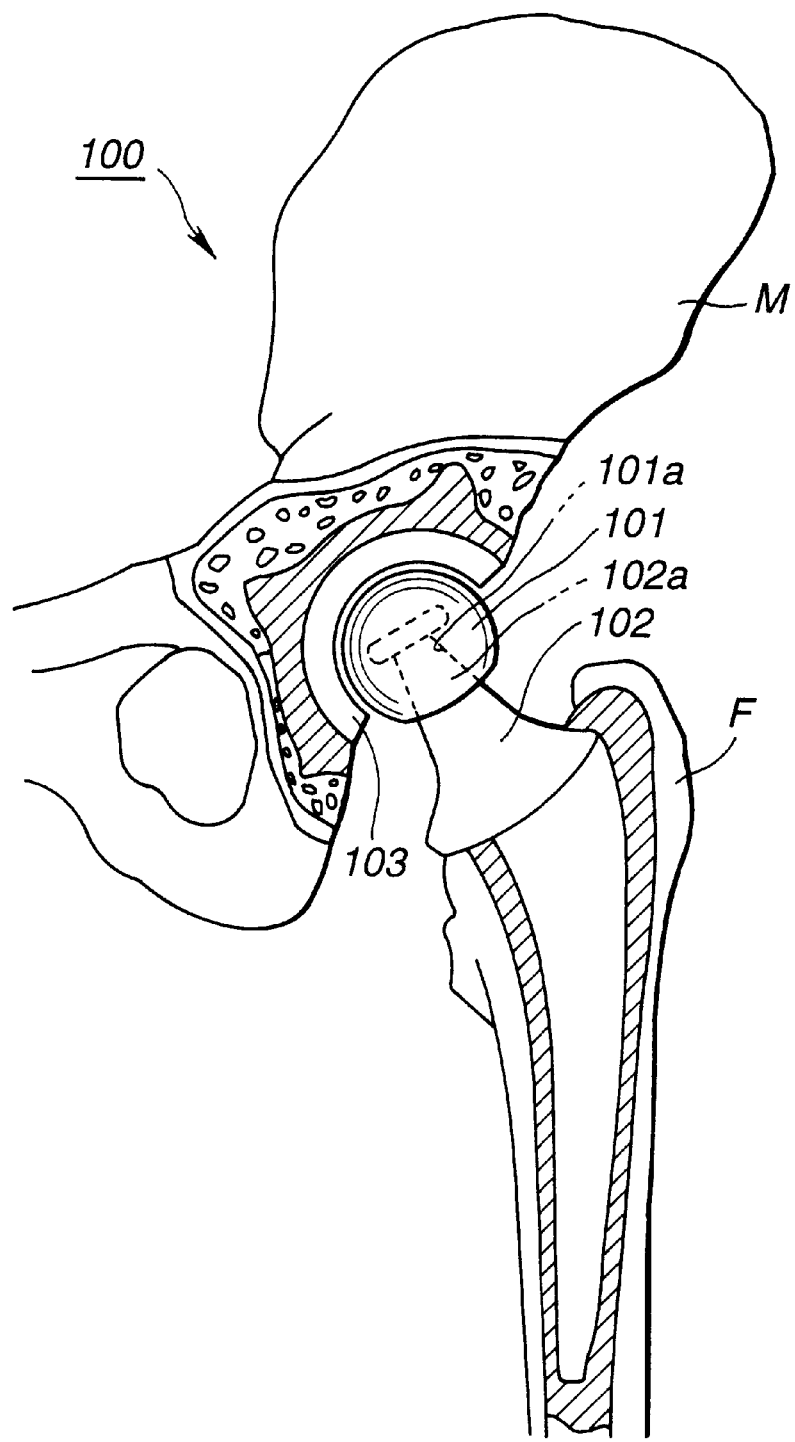
FIG. 5 is a view similar to FIG. 2 but shows a prior art femur head.

Further, as shown in FIG. 4, in the state of the stem 4 being fitted into the femur head and under the condition where the sliding surface 3d of the femur head 3 is supported on a conical block 21 by way of a steel ring 22, a load in the axial direction of the stem 4 was applied to the femur head 3 by means of a compression test machine, and the load that caused the femur head 3 to start breaking was determined as the compression rupture strength. The result was also shown in Table 3.

TABLE 1

| Example No. | Material of Femur Head | Surface Finish on Femur Head Side | Material of Stem | Surface Finish on Stem Side [μm] | Difference in Degree of Surface Finish |
|---|---|---|---|---|---|
| Invention | | | | | |
| 1 | $Al_2O_3$-base Ceramic | Ra: 0.06 Rmax: 0.51 | Ti alloy | Ra: 0.11 Rmax: 0.91 | 0.05 0.40 |
| 2 | $Al_2O_3$-base Ceramic | Ra: 0.12 Rmax: 1.03 | Ti alloy | Ra: 0.21 Rmax: 1.50 | 0.09 0.47 |
| 3 | $Al_2O_3$-base Ceramic | Ra: 0.42 Rmax: 4.01 | Ti alloy | Ra: 0.92 Rmax: 7.04 | 0.50 3.03 |
| 4 | $Al_2O_3$-base Ceramic | Ra: 0.95 Rmax: 10.00 | Ti alloy | Ra: 0.15 Rmax: 2.04 | 0.80 7.96 |
| 5 | $ZrO_2$-base Ceramic | Ra: 0.41 Rmax: 3.52 | Ti alloy | Ra: 0.35 Rmax: 3.01 | 0.06 0.51 |
| 6 | $Al_2O_3$-base Ceramic | Ra: 0.75 Rmax: 6.53 | Stainless Steel | Ra: 0.70 Rmax: 7.54 | 0.05 1.01 |
| 7 | $ZrO_2$-base Ceramic | Ra: 0.75 Rmax: 6.52 | Stainless Steel | Ra: 0.71 Rmax: 7.54 | 0.04 1.02 |
| 8 | $Al_2O_3$-base Ceramic | Ra: 0.91 Rmax: 9.52 | Co—Cr alloy | Ra: 0.95 Rmax: 10.00 | 0.04 0.48 |
| 9 | $ZrO_2$-base Ceramic | Ra: 0.90 Rmax: 9.51 | Co—Cr alloy | Ra: 0.95 Rmax: 10.00 | 0.05 0.49 |
| 10 | $Al_2O_3$-base Ceramic | Ra: 0.04 Rmax: 0.43 | Ti alloy | Ra: 0.54 Rmax: 5.01 | 0.50 4.58 |
| 11 | $ZrO_2$-base Ceramic | Ra: 0.04 Rmax: 0.41 | Ti alloy | Ra: 0.54 Rmax: 5.03 | 0.50 4.62 |
| 12 | $ZrO_2$-base ceramic | Ra: 0.04 Rmax: 0.40 | Stainless Steel | Ra: 0.54 Rmax: 5.04 | 0.50 4.64 |

TABLE 2

| Example No. | Material of Femur Head | Surface Finish on Femur head Side | Material of Stem | Stem side Surface Finish [μm] | Difference in Degree of Surface Finish |
|---|---|---|---|---|---|
| Comparative Examples | | | | | |
| 13 | $Al_2O_3$-base Ceramic | Ra: 0.51 Rmax: 4.52 | Ti alloy | Ra: 1.55 Rmax: 16.03 | 1.04 11.51 |
| 14 | $Al_2O_3$-base Ceramic | Ra: 1.10 Rmax: 10.22 | Ti alloy | Ra: 0.00* Rmax: 0.03 | 1.10 10.19 |
| 15 | $Al_2O_3$-base Ceramic | Ra: 1.10 Rmax: 10.22 | Co—Cr alloy | Ra: 0.00 Rmax: 0.03 | 1.10 10.19 |
| 16 | $ZrO_2$-base Ceramic | Ra: 1.12 Rmax: 10.19 | Co—Cr alloy | Ra: 0.00 Rmax: 0.03 | 1.12 10.16 |

*The stem side surface finish (i.e., surface roughness Ra) being zero means that the measured value is smaller than the minimum scale of the measuring machine so that the surface is so smooth as to be actually immeasurable.

TABLE 3

| Example No. | Ground State of Femur Head | Condition at the time of Fitting | Breakage at the time of Fitting | Compression Rupture Strength [Kgf] |
|---|---|---|---|---|
| Invention | | | | |
| 1 | Grinding amount being small | Easily fitted | No breakage | 7100 |
| 2 | ↑ | ↑ | ↑ | 6300 |
| 3 | ↑ | ↑ | ↑ | 6100 |
| 4 | ↑ | ↑ | ↑ | 6250 |
| 5 | ↑ | ↑ | ↑ | 8500 |
| 6 | ↑ | ↑ | ↑ | 5250 |
| 7 | ↑ | ↑ | ↑ | 6750 |
| 8 | ↑ | ↑ | ↑ | 4700 |
| 9 | ↑ | ↑ | ↑ | 5900 |
| 10 | Grinding amount being large | ↑ | ↑ | 3600 |
| 11 | ↑ | ↑ | ↑ | 4800 |
| 12 | ↑ | ↑ | ↑ | 2850 |
| Comparative Examples | | | | |
| 13 | Grinding amount being small | Take time for fitting | ↑ | 2150 |
| 14 | ↑ | ↑ | ↑ | 1700 |
| 15 | ↑ | ↑ | ↑ | 2000 |
| 16 | ↑ | ↑ | ↑ | 2700 |

By mark "↑" is represented "ditto".

In the meantime, in Tables 2 and 3, a $ZrO_2$ system indicates a femur head that was shaped similarly to that of the embodiment and was made by using a mixed powder of ZrO, $ZrO_2$ and $Y_2O_3$ serving as a stabilizing component.

From Tables 1–3, it is apparent that in case of the examples of Nos. 1–9 in which the inner peripheral surface of the taper hole 3b of the ceramic femur head 3 and the outer peripheral surface of the tapered portion 4a of the metallic stem 4 are substantially the same in the degree of surface finish (i.e., in the surface roughness), and in which the difference in the degree of surface finish is 1 μm in Ra (center line average roughness according to JIS 0601) or less and 10 μm Rmax (maximum height according to JIS 0601) or less while the degree of surface finish is in the range from 0.05 to 1.0 μm Ra and in the range from 0.5 to 10 μm Rmax, there can be attained a marked effect that smooth fitting is attained, no breakage is caused in the ceramic femur head 3 at the time of its fitting and the compression rupture strength is quite large.

Accordingly, by using such a femur system 2, it becomes possible to attain an artificial hip joint 1 which is small-sized and has a sufficient strength with ease.

Further, the degree of surface finish on the ceramic femur head 3 side can be lower than the conventional, notwithstanding such an excellent effect can be attained, there results an advantage that the working process can be simplified.

In the meantime, the examples of Nos. 10–12 requires a more grounded amount (i.e., more grinding work or effort) for making higher the degree of finish on the femur head side, as compared with the examples of Nos. 1–9 but can attain a larger compression rupture strength since smaller in the difference in the degree of surface finish (i.e., the difference in the surface roughness).

In contrast to the examples of Nos. 1–12, the comparative examples is so large in the difference in the degree of surface finish, i.e., the difference is larger than 1 μm Ra and 10 μm Rmax, and small in the compression rupture strength and thus not desirable. Further, regarding the fitting condition, the comparative examples which are lower particularly in the degree of surface finish on the femur head side (i.e., the comparative examples of Nos. 14–16) cannot attain smooth fitting and requires much time in their fitting since their outer surface is rough. Furthermore, the comparative examples have a large tendency that they are actually brought into a point contact with the metallic stem and therefore not desirable. In the meantime, the example No. 13 is smooth at the femur head side surface but rough at the stem side surface, so fitting in its assembly is not smooth and requires much time.

While the present invention has been described and shown as above, it is not for the purpose of limitation but various modifications and variations can be made thereto without departing from the scope of the appended claims.

What is claimed is:

1. A femur system comprising:
   a ceramic femur head having a tapered bore tapering toward an inner end thereof; and
   a stem having a tapered stem portion tapering toward a terminal end thereof and fitted in said tapered bore of said ceramic femur head;
   wherein an inner peripheral surface of said tapered bore of said ceramic femur head has substantially the same surface roughness as an outer peripheral surface of said tapered stem portion of said stem.

2. A femur system according to claim 1, wherein the difference in the surface roughness between said outer peripheral surface of said tapered stem portion of said stem and said inner peripheral portion of said tapered bore of said ceramic femur head is less than 1 μm Ra.

3. A femur system according to claim 1, wherein the difference in the surface roughness between said outer peripheral surface of said tapered stem portion of said stem and said inner peripheral portion of said tapered bore of said ceramic femur head is less than 10 μm Rmax.

4. A femur system according to claim 1, wherein said inner peripheral surface has a surface roughness in the range from 0.05 to 1.0 μm Ra.

5. A femur system according to claim 1, wherein said inner peripheral surface has a surface roughness in the range from 0.5 to 10 μm Rmax.

* * * * *